United States Patent
Newell et al.

(10) Patent No.: US 6,660,254 B1
(45) Date of Patent: Dec. 9, 2003

(54) LEAVE-IN FOAMING COMPOSITION FOR CONDITIONING, LIGHTENING AND HIGHLIGHTING HAIR

(75) Inventors: Gerald Newell, Hoffman Estates, IL (US); Charles Montgomery, Jr., Chicago, IL (US); Richard Abbott, Downers Grove, IL (US)

(73) Assignee: Unilever Home & Personal Care USA, division of Conopco, Inc., Chicago, IL (US)

( * ) Notice: Subject to any disclaimer, the term of this patent is extended or adjusted under 35 U.S.C. 154(b) by 0 days.

(21) Appl. No.: 09/566,114

(22) Filed: May 5, 2000

(51) Int. Cl.[7] .................. A61K 31/74; A61K 7/00; A61K 9/00
(52) U.S. Cl. .................. 424/70.28; 424/47; 424/70.27; 424/70.6; 424/70.19
(58) Field of Search ................ 424/64, 70, 70.1, 424/70.6, 70.27, 70.28, 47

(56) References Cited

U.S. PATENT DOCUMENTS

| | | | |
|---|---|---|---|
| 2,438,091 A | | 3/1948 | Lynch |
| 2,528,378 A | | 10/1950 | Mannheimer et al. |
| 2,658,072 A | | 11/1953 | Kosmin |
| 3,709,437 A | | 1/1973 | Wright |
| 3,950,417 A | | 4/1976 | Verdicchio et al. |
| 4,018,364 A | | 4/1977 | Wright |
| 4,511,486 A | | 4/1985 | Shah |
| 4,656,043 A | | 4/1987 | Hawkins et al. |
| 5,120,531 A | * | 6/1992 | Wells et al. ................ 424/70 |
| 5,376,643 A | * | 12/1994 | Sugiyama et al. ......... 424/70.6 |
| 5,948,739 A | * | 9/1999 | Inman .................... 424/70.12 |
| 5,968,486 A | | 10/1999 | Newell et al. |
| 6,143,286 A | * | 11/2000 | Bhambhani et al. ........ 424/407 |

FOREIGN PATENT DOCUMENTS

| | | |
|---|---|---|
| EP | 0437075 | 7/1991 |
| WO | 93/14024 | 7/1993 |

* cited by examiner

*Primary Examiner*—Thurman K. Page
*Assistant Examiner*—Robert M. Joynes

(57) ABSTRACT

There is described an aqueous, foamable composition delivered from a foaming device for conditioning, lightening and highlighting hair which comprises:

(i) a conditioning agent,
(ii) a peroxygen compound,
(iii) an acid, and
(iv) a foaming agent;
said composition having a pH of 5 or less.

There is also described a method for conditioning lightening and highlighting hair which comprises treating said hair with a composition of the invention.

7 Claims, No Drawings

LEAVE-IN FOAMING COMPOSITION FOR CONDITIONING, LIGHTENING AND HIGHLIGHTING HAIR

BACKGROUND OF THE INVENTION

It is known within the art to lighten and highlight hair with a peroxygen compound such as hydrogen peroxide. An object of the present invention, is to provide foamed conditioners which contain stable peroxygen compounds and thus can be used as hair lighteners and highlighters as well as conditioners.

Current products on the market for lightening hair come in two forms. The first is a spray leave-on peroxide solution. This product is used occasionally when the hair will be exposed to sunlight after application. Examples of such products include Super Sun-In®, Super With Lemon Sun-In®, and Gradual Sun-In For Men®. Super Sun-In® has about 1.9% hydrogen peroxide at a pH of about 4.0. Super With Lemon Sun-In® has about 3.7% hydrogen peroxide at a pH of about 4.0. Gradual Sun-In For Men® has about 3.7% hydrogen peroxide at a pH of about 3.

The second product for lightening hair is a system which has two components: a bleaching component such as hydrogen peroxide and another component which is a bleach oil or powder. This system requires two containers and/or two bottles, one for each of the components. These products will lighten and highlight the hair, however, often the result is damage that leaves hair in a less than healthy state.

It is known to prepare an unstable composition by combining a bleach with a shampoo or conditioner and immediately thereafter applying the resulting composition to the hair. This is usually done in a hair salon and will result in the immediate lightening of the hair. By contrast, stable conditioner compositions which gradually lighten and highlight the hair and which can easily be used at home are provided by the present invention.

Publications and patent documents which relate to the area of technology of the invention are as follows:

WO 93/14024 A1 (1993) discloses a hair care composition comprising (a) about 3–8% of a water soluble or dispersible alkylated polyvinylpyrrolidone copolymer powder comprising: (i) about 90–95% polyvinylpyrollidone having a K-value of 30–90, and (ii) 5–10% of an alkylene having 4 carbon atoms; (b) about 50–95% water; and (c) about 0–60% alcohol.

U.S. Pat. No. 4,656,043 (1987) discloses a stable aqueous hair conditioning shampoo comprising an aqueous solution of hydrogen peroxide, a specific anionic surfactant, at least one nonionic surfactant, an acidic pH-producing agent and one or more hair conditioning components.

EP 437,075 A (1990) relates to the use of acrylic functional siloxanes that are useful in the perming and conditioning of hair.

U.S. Pat. No. 5,968,486 (1999) discloses a shampoo composition for lightening and highlighting hair which comprises i) a peroxygen compound, and ii) an anionic sulfonate;

said composition having a pH of 5 or less.

U.S. Ser. No. 09/138,189 filed Aug. 21, 1998, commonly assigned, and pending, discloses a conditioning composition for lightening and highlighting hair which comprises i) a peroxygen compound, and ii) a conditioning agent;

said composition having a pH of about 5 or less.

SUMMARY OF THE INVENTION

The invention relates to a leave on aqueous, foamable composition delivered from a foaming device for conditioning, lightening and highlighting hair which comprises:

(i) a conditioning agent, (ii) a peroxygen compound, (iii) an acid, and (iv) a foaming agent;

said composition having a pH of about 5 or less.

The invention is also directed to a method for lightening and highlighting hair which comprises administering to the hair an effective amount of a composition of the invention.

The peroxygen compound makes the conditioner composition a lightening and hair highlighting composition. Peroxygen compounds are not stable in conditioners at pH's of above 5. The composition is made acidic by addition of a acid, such as a mineral acid, like phosphoric acid or sulfuric acid, or an organic acid like citric acid.

DETAILED DESCRIPTION OF THE INVENTION

As used herein % means weight % of the total composition unless otherwise designated. "A portion of a head of hair" means some but not all of the hair on a head. It is understood that compositions of the invention can be used to highlight and/or lighten a portion of a head of hair in a pattern so as to conform to certain styles of hair highlighting and/or lightening. The compositions of the invention can also be used to highlight and lighten a whole head of hair. The compositions of the invention are made using known ingredients or with ingredients analogous to those known in the art. The packages to be used with compositions of the invention are made using known processes and materials or by processes and materials which are analogous to those known in the art.

There are two methods to lighten and highlight hair. The first method is to deposit onto the hair, molecules which color the hair. The second method is to bleach the natural pigment found in the hair. The present invention relates to the latter method.

Hair contains a number of different pigments, principally brown and red. When hair is bleached by chemicals or the sun, the brown pigments react faster, and therefore disappear faster than the red pigments. The change in the red to brown ratio changes the appearance of the hair giving more red shading to the natural color of the hair. This results in the lightening of the hair. The red color that appears is perceived as highlighting of the hair.

Peroxygen compounds such as hydrogen peroxide, melamine peroxide, and urea peroxide, have been used to bleach human hair. Persulfates such as ammonium, sodium, and potassium persulfate may be used. Perborates such as sodium may also be used. The preferred peroxygen compound is hydrogen peroxide. Hydrogen peroxide is stable, but will decompose under the appropriate conditions to form water and an active species of oxygen. The active species of oxygen is very reactive. It attacks and decolorizes the hair pigment.

It has been found that a peroxygen compound, preferably hydrogen peroxide, is stable in a foaming conditioner composition when present in about a 0.01 wt. % to about 10 wt. % (preferably 2%) in the presence of an acid so as to make the pH of the foam about 5 or less.

In the compositions of the present invention, any acid that can result in a pH of 5 or less may be employed. More specifically, any acid which has a pK such that it can be used to obtain a composition with a pH of 5 or less, may be employed. Exemplary of such acids are any mineral acid such as sulfuric acid or phosphoric acid. Appropriate organic acids such as citric acid may also be used.

The invention relates to a leave on aqueous, foamable composition delivered from a foaming device, for lightening and highlighting hair which comprises:

(i) a conditioning agent, (ii) a peroxygen compound, (iii) an acid, and (iv) a foaming agent, said composition having a pH of about 5 or less.

The invention is also directed to a method for lightening and highlighting hair which comprises administering to the hair a lightening and highlighting effective amount of the aqueous, foamable, conditioning composition described above.

Ingredients used in the compositions of the invention are described below.

Conditioning Agent

A conditioning agent which may be included in the compositions of the invention, can be a quaternary amine compound of the formula:

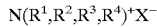

wherein $R^1$ and $R^2$ are long chain aliphatic hydrocarbon radicals, that is alkyl radicals, having about 10 to about 26 carbon atoms, and preferably about 12 to about 18 carbons, and $R^3$ and $R^4$ are hydrogen, lower alkyl radicals having about 1 to about 5 carbon atoms with the proviso that no more than three of the substituents on the nitrogen can be hydrogen, and with the further proviso that the total number of carbon atoms in the substituents on the nitrogen equals at least 60.

More specifically, the substituents $R^1$, $R^2$, $R^3$, and $R^4$ may be selected from the group consisting of hydrogen, ethyl methyl, n-propyl, i-propyl, n-butyl, sec-butyl, tert-butyl, n-pentyl, n-decyl, lauryl, myristyl, palmityl, stearyl, behenyl, palmitoleyl, oleyl, linoleyl, linelenyl, erucyl, and the like. $X^-$ may be an inorganic or organic ion, including, but not limited to, hydroxide, chloride, bromide, iodide, fluoride, sulfate, phosphate, sulfonate, alkanoate such as acetate, n-propionate, lactate and gluconate; and lower alkyl sulfate.

To more particularly illustrate the quaternary amine compounds that may be used, without limiting the scope of these compounds, mention may be made of the following:

stearyltrimethylammonium chloride;
behenetrimethylammonium chloride;
cetrimonium chloride;
soytrimonium chloride;
tallowtrimonium chloride;
dihyrogenatedtallowdimethylammonium chloride;
behentrimethylammonium methosulfate;
PEG-2 Olealmonium chloride;
dihyrogenatedtallowdimethylammonium bromide;
dihyrogenatedtallowdimethylammonium methosulfate;
palmityltrimethylammonium chloride;
hydrogenated tallowtrimethylammonium chloride;
hydrogenated tallowtrimethylammonium bromide;
dicetyldimethylammonium chloride;
distearyldimethylammonium chloride;
dipalmityldimethylammonium chloride;
hydrogenated tallowtrimethylammonium methosulfate;
cetrimonium tosylate;
eicosyltrimethylammonium chloride,
ditallowdimethylammonium chloride,
cetyl pyridinium chloride,
lauryl trimethyl ammonium bromide,
lauryl amine stearyl amine rosin amine,
N-dodecyl ethanoldiamine,
N-alkyl trimethyl ammonium chloride, and
lauryl trimethyl ammonium chloride.

The preferred conditioner is cetrimonium chloride.

Other types of conditioning agents which may be used in compositions of the invention are polysiloxane conditioners, such as polysiloxane polyether copolymer, diquaternary polydimethyl silicone, and polysiloxane, polyorgano thiosulfate; silicone polyol sulfosuccinates such as disodium silicone polyol sulfosuccinate, disodium oleamide MEA sulfosuccinate, and disodium ricinoleyl MEA sulfosuccinate; and cationic conditioning polymers.

The conditioning compositions of the present invention can comprise an organic, cationic polymer as a hair conditioning agent. Suitable polymers are those known cationic polymers that provide conditioning benefits to hair. Such cationic polymers should also be physically and chemically compatible with the essential components described herein, or should not otherwise unduly impair product stability, aesthetics or performance.

The concentration of the organic, cationic, conditioning polymer of the conditioning composition should be sufficient to provide the desired conditioning benefits. Such concentrations generally range from about 0.025% to about 3%, preferably from about 0.05% to about 2%, more preferably from about 0.1% to about 1%, by weight of the conditioning composition.

The cationic conditioning polymer contains cationic nitrogen-containing moieties such as quaternary ammonium or cationic protonated amino moieties. The cationic protonated amines can be primary, secondary, or tertiary amines (preferably secondary or tertiary), depending upon the particular species and the selected pH of the conditioning composition. The average molecular weight of the cationic conditioning polymers is between about 10 million and about 5,000, preferably at least about 100, 000, more preferably at least about 200,000, but preferably not more than about 2 million, preferably not more than about 1.5 million. The polymers can also have a cationic charge density ranging from about 0.2 meq/gm to about 7 meq/gm, preferably at least about 0.4 meq/gm, more preferably at least about 0.6 meq/gm, but also preferably less than about 5 meq/gm, more preferably less than about 2 meq/gm, at the pH of intended use of the conditioning composition.

Any anionic counterions can be use in association with the cationic conditioning polymers so long as the polymers remain soluble in water, in the conditioning composition, or in a coacervate phase of the conditioning composition, and so long as the counterions are physically and chemically compatible with the essential components of the conditioning composition or do not otherwise unduly impair product performance, stability or aesthetics. Non limiting examples of such counterions include halides (e.g., chlorine, fluorine, bromine, iodine), sulfate and methylsulfate.

The cationic nitrogen-containing moiety of the cationic polymer is generally present as a substituent on all, or more typically on some, of the monomer units thereof. Thus, the cationic polymer for use in the conditioning composition includes homopolymers, copolymers, terpolymers, and so forth, of quaternary ammonium or cationic amine-substituted monomer units, optionally in combination with non-cationic monomers referred to herein as spacer monomers. Non limiting examples of such polymers are described in the CTFA Cosmetic Ingredient Dictionary, 3rd edition, edited by Estrin, Crosley, and Haynes, (The Cosmetic, Toiletry, and Fragrance Association, Inc., Washington, D.C. (1982), which description is incorporated herein by reference.

Non limiting examples of suitable cationic polymers include copolymers of vinyl monomers having cationic protonated amine or quaternary ammonium functionalities with water soluble spacer monomers such as acrylamide, methacrylamide, alkyl and dialkyl acrylamides, alkyl and dialkyl methacrylamides, alkyl acrylate, alkyl methacrylate, vinyl caprolactone or vinyl pyrrolidone. The alkyl and dialkyl substituted monomers preferably have from C1 to C7 alkyl groups, more preferably from C1 to C3 alkyl groups. Other suitable spacer monomers include vinyl esters, vinyl alcohol (made by hydrolysis of polyvinyl acetate), maleic anhydride, propylene glycol, and ethylene glycol.

Suitable cationic protonated amino and quaternary ammonium monomers, for inclusion in the cationic polymers of the composition herein, include vinyl compounds substituted with dialkylaminoalkyl acrylate, dialkylaminoalkyl methacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidone, e.g., alkyl vinyl imidazolium, alkyl vinyl pyridinium, alkyl vinyl pyrrolidone salts. The alkyl portions of these monomers are preferably lower alkyls such as the C1, C2 or C3 alkyls.

Suitable amine-substituted vinyl monomers for use herein include dialkylaminoalkyl acrylate, dialkylaminoalkyl methacrylate, dialkylaminoalkyl acrylamide, and dialkylaminoalkyl methacrylamide, wherein the alkyl groups are preferably C1–C7 hydrocarbyls, more preferably C1–C3, alkyls.

Other suitable cationic polymers for use in the conditioning composition include copolymers of 1-vinyl-2-pyrrolidone and 1-vinyl-3-methylimidazolium salt (e.g., chloride salt) (referred to in the industry by the Cosmetic, Toiletry, and Fragrance Association, "CTFA", as Polyquaternium-16), such as those commercially available from BASF Wyandotte Corp. (Parsippany, N.J., U.S.A.) under the LUVIQUAT trade name (e.g., LUVIQUAT FC 370); copolymers of 1-vinyl-2-pyrrolidone and dimethylaminoethyl methacrylate (referred to in the industry by CTFA as Polyquaternium-11) such as those commercially available from ISP Corporation (Wayne, N.J., U.S.A.) under the GAFQUAT trade name (e.g., GAFQUAT 755N); cationic diallyl quaternary ammonium-containing polymers, including, for example, dimethyldiallylammonium chloride homopolymer and copolymers of acrylamide and dimethyldiallylammonium chloride, referred to in the industry (CTFA) as Polyquaternium 6 and Polyquaternium 7, respectively; and mineral acid salts of amino-alkyl esters of homopolymers and copolymers of unsaturated carboxylic acids having from 3 to 5 carbon atoms, as described in U.S. Pat. No. 4,009,256, which description is incorporated herein by reference.

Other suitable cationic polymers for use in the conditioning composition include polysaccharide polymers, such as cationic cellulose derivatives and cationic starch derivatives.

Preferred cationic cellulose polymers are those polymers available from of Amerchol Corp. (Edison, N.J., USA) in their Polymer JR and LR series of polymers, as salts of hydroxyethyl cellulose reacted with trimethyl ammonium substituted epoxide, referred to in the industry (CTFA) as Polyquaternium 10.

Other suitable cationic polymers include cationic guar gum derivatives, such as guar hydroxypropyltrimonium chloride, specific examples of which include the Jaguar series commercially available from Celanese Corporation.

Preferred examples of cationic polymers include: Polymer JR 30M and Polyquaternium—10.

A Peroxygen Compound

Peroxygen compounds such as hydrogen peroxide, melamine peroxide, and urea peroxide, have been used to bleach human hair. Persulfates such as ammonium, sodium, and potassium persulfate may be used. Perborates such as sodium may also be used. The preferred peroxygen compound is hydrogen peroxide. Hydrogen peroxide is stable, but will decompose under the appropriate conditions to form water and an active species of oxygen. The active species of oxygen is very reactive. It attacks and decolorizes the hair pigment.

An Acid

As noted above, the peroxygen compound makes the conditioner composition a lightening and hair highlighting composition; however, peroxygen compounds are not stable in conditioners at pH's of above 5, but are stable at pH's of about 5 or less. Therefore, the composition is made acidic by addition of a acid, such as a mineral acid, like phosphoric acid or sulfuric acid, or an appropriate organic acid such as citric acid.

Foaming Agent

Compositions of the present invention are foamable compositions, and they include a foaming agent. Any foaming agent except anionic foaming agents, may be employed in the compositions of the invention. Anionic foaming agents are not suitable for use in compositions of the invention because they can react or complex with the cationic conditioning agents that are present to reduce the good hair care properties of the resulting conditioning composition. Cationic foaming agents which are suitable for use in compositions of the invention, may also serve in a second function, as the conditioning agent.

The different types of foaming agent which may be employed in the compositions of the invention are now described.

The different types of foaming agents are cationic surfactants, nonionic surfactants, zwitterionic surfactants and amphoteric surfactants.

Cationic Surfactants

Nonlimiting examples of cationic surfactants are quaternary ammonium compounds, which are listed above, and which can also serve as foaming agents. Most preferred among these cationic quaternary ammonium compounds are cetrimonium chloride, PEG-2 Olealmonium chloride, and mixtures thereof.

Nonionic Surfactants

Nonionic surfactants which may be used as foaming agents in compositions of the invention include esters formed between 1 mol of polyhydric alcohol containing two to six hydroxyl groups and at least 1 mol of a monobasic carboxylic acid containing 7 to 18 carbon atoms in its structures. Nonlimiting examples of nonionic surfactants which may be used include ethylene glycol monolaurate, glyceryl monolaurate, pentaerythritol monolaurate, sorbitan monopalmitate, sorbitan monostearate, sorbitan distearate; ethylene oxide condensates of the partial fatty acid esters of polyhydric alcohols described above; 7 to 18 carbon atom monohydric alcohols, ethylene oxide condensates of reactive hydrogen compounds containing 7 to 18 carbon atoms in their structure, that is, long chain fatty alcohols such as lauryl alcohol and stearyl alcohol; the long chain fatty acids such as myristic acid, stearic acid, and the rosin acids.

Nonionic surfactants such as PEG glyceryl fatty esters can be used as foaming surfactants. They can be used in combination with an amphoteric, or zwitterionic surfactant, or mixtures thereof. Examples of classes of nonionic surfactants are:
1. The polyethylene oxide condensates of alkyl phenols,
2. Those derived from the condensation of ethylene oxide with the product resulting from the reaction of propylene oxide and ethylene diamine products which may be varied in composition depending upon the balance between the hydrophobic and hydrophilic elements which is desired.
3. The condensation product of aliphatic alcohols having from about 8 to about 18 carbon atoms, in either straight chain or branched chain configuration, with ethylene oxide.
4. Long chain tertiary amine oxides. Nonlimiting examples of amine oxides suitable for use in this invention include, dimethyldodecylamine oxide, oleyldi(2-hydroxyethyl) amine oxide, dimethyloctylamine oxide, dimethyldecylamine oxide, and dimethyl-tetradecyl-amine oxide.
5. Long chain tertiary phosphine oxides.
   Nonlimiting examples of suitable phosphine oxides are: dodecyidimethylphosphine oxide and tetradecyldimethylphosphine oxide.
6. Long chain dialkyl sulfoxides containing one short chain alkyl or hydroxy alkyl radical of from about 1 to about 3 carbon atoms (usually methyl) and one long hydrophobic chain which include alkyl, alkenyl, hydroxy alkyl, or keto alkyl radicals containing from about 8 to about 20 carbon atoms, from 0 to about 10 ethylene oxide moieties and from 0 to about 1 glyceryl moiety. Nonlimiting examples include: octadecyl methyl sulfoxide, 2-ketotridecyl methyl sulfoxide; and 3,6,9,-trixaoctadecyl 2-hydroxyethyl sulfoxide; dodecyl methyl sulfoxide.
7. Other nonionic surfactants can also be used in the compositions hereof. Polysorbates, e.g., sucrose esters of fatty acids; alkyl polysaccharide nonionic surfactants which are disclosed in U.S. Pat. No. 4,565,647, Llenado, issued Jan. 21, 1986, having a hydrophobic group containing from about 6 to about 30 carbon atoms, preferably from about 10 to about 16 carbon atoms and a polysaccharide, e.g., a polyglycoside, hydrophilic group.

The alkyl polysaccharides include alkylpolyglycosides. The glycosyl can be derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4- and/or 6-position, preferably predominantly the 2-position.

Zwitterionic Surfactants

Zwitterionic surfactants are exemplified by those which can be broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms.

Examples of such surfactants include:
4-[N,N-di(2-hydroxyethyl)-N-octadecylammonio]-butane-1-carboxylate;
5-[S-3-hydroxypropyl-S-hexadecylsulfonio]-3-hydroxypentane-1-sulfate;
3-[P,P-diethyl-P-3,6,9-trioxatetradexocylphosphonio]-2-hydroxy-propane-1-phosphate;
3-[N,N-dipropyl-N-3-dodecoxy-2-hydroxypropylammonio]-propane-1-phosphonate;
3-(N,N-dimethyl-N-hexadecylammonio)propane-1-sulfonate;
3-(N,N-dimethyl-N-hexadecylammonio)-2-hydroxypropane-1-sulfonate;
4-[N,N-di(2-hydroxyethyl)-N-(2-hydroxydodecyl) ammonio]-butane-1-carboxylate;
3-[S-ethyl-S-(3-dodecoxy-2-hydroxypropyl)sulfonio]-propane-1-phosphate;
3-[P,P-dimethyl-P-dodecylphosphonio]-propane-1-phosphonate; and
5-[N,N-di(3-hydroxypropyl)-N-hexadecylammonio]-2-hydroxy-pentane-1-sulfate.

Other zwitterionics such as betaines can also be useful in the present invention. Examples of betaines useful herein include the high alkyl betaines, such as coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alphaecarboxyethyl betaine, cetyl dimethyl carboxymethyl betaine, lauryl bis-(2-hydroxyethyl)carboxymethyl betaine, stearyl bis-(2- hydroxypropyl)carboxymethyl betaine, oleyl dimethyl gamma-carboxypropyl betaine, and lauryl bis-(2-hydroxypropyl)alpha-carboxyethyl betaine.

The sulfobetaines may be represented by coco dimethyl sulfopropyl betaine, stearyl dimethyl sulfopropyl betaine, lauryl dimethyl sulfoethyl betaine, lauryl bis-(2-hydroxyethyl)sulfopropyl betaine and the like.

Amidobetaines are also useful in this invention. Preferred betaines for use in the present compositions are cocoamidopropyl betaine, cocobetaine, lauryl amidopropyl betaine, and oleyl betaine.

Amphoteric Surfactants

Amphoteric surfactants can also be used as foaming agents in compositions of the invention. Examples of amphoteric surfactants which can be used in the compositions of the present invention are those which are broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecyl-aminopropionate, sodium 3-dodecylaminopropane sulfonate, sodium lauryl sarcosinate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products sold under the trade name "Miranol" and described in U.S. Pat. No. 2,528, 378.

Other amphoteric surfactants include sultaines and amidosultaines. Sultaines and amidosultaines can advantageously be utilized as foam enhancing surfactants that are mild to the eye in partial replacement of anionic surfactants. Sultaines, including amidosultaines, include for example, cocodimethylpropylsultaine, stearyldimethylpropylsultaine, lauryl-bis-(2-hydroxyethyl)propylsultaine and the like; and the amidosultaines such as cocoamidodimethylpropylsultaine, stearylamidododimethylpropylsultaine, laurylamidobis-(2-hydroxyethyl)propylsultaine, and the like. Preferred are amidohydroxysultaines such as the C12–C18 hydrocarbyl amidopropyl hydroxysultaines, especially C12–C14 hydrocarbyl amido propyl hydroxysultaines, e.g., laurylamidopropyl hydroxysultaine and cocamidopropyl hydroxysultaine. Other sultaines are disclosed in U.S. Pat. No. 3,950,417, issued Apr. 13, 1976, incorporated herein by reference.

Other specific amphoterics include imidazolinium materials.

Specific commercial products providing the imidazolinium derivative component of the present compositions include those sold under the trade names of MIRANOL C2M CONC. N.P., MIRANOL C2M CONC. O.P., MIRANOL C2M SF, MIRANOL CM SPECIAL (Miranol, Inc.); ALKATERIC 2CIB (Alkaril Chemicals); AMPHOTERGE W-2 (Lonza, Inc.); MONATERIC CDX-38, MONATERIC CSH-32 (Mona Industries); REWOTERIC AM-2C (Rewo Chemical Group); and SCHERCOTIC MS-2 (Scher Chemicals).

Another specific class of amphoteric surfactants is defined by the aminoalkanoates.

Examples of amphoteric surfactants include n-alkylamino-propionates and n-alkyliminodipropionates. Such materials are sold under the trade name DERIPHAT by Henkel and MIRATAINE by Miranol, Inc. Specific examples include N-lauryl-beta-amino propionic acid or salts thereof, and N-lauryl-beta-amino-dipropionic acid (DERIPHAT 160C) or salts thereof, and mixtures thereof. surfactants, or a mixture thereof.

Aqueous Carrier

The carrier of the conditioning composition is predominantly water. Deionized water is often employed.

Optional Ingredients Which may be Used in Compositions of the Invention

In addition to the above-described ingredients, other common cosmetic components and additives can be incorporated in the conditioning composition with the ingredients, as long as the basic properties of the composition, and an ability to condition the hair, are not adversely affected. Such optional ingredients include, but are not limited to, humectants, inorganic salts, fragrances, hydrotropes, preservatives, water softening agents, acids, bases, buffers and the like. Optional components usually are present in weight percentages of less than about 2% each, and from about 5% to about 10% by weight of the composition in total.

Other optional materials that can be used in compositions of the invention include fatty esters, polymers, such as styrene polymers, and fatty alcohols. The compositions of the invention may further comprise hexamethyldisiloxane or cyclomethicone.

Foaming Packages or Containers Which may be Used in Compositions of the Invention In order to conveniently produce the aerated foams of this invention, a suitable non-pressurized foam container such as that described in U.S. Pat. No. 3,709,437 which is hereby incorporated by reference, can be employed. The composition can be placed into the reservoir of a plastic squeeze bottle which contains a foamer head or other foam producing means. Squeezing the container causes the solution to leave the reservoir and enter an air-mixing or foaming chamber via an internal dip tube. The foam produced in the foaming chamber is often passed through a homogenizing element interposed between the air-mixing chamber and the discharge orifice to homogenize and control the consistency of the discharged foam. Further compression of the foam discharges the foam from a discharge cap as a uniform non-pressurized aerated foam. Alternatively the side walls of the container may be rigid and the dip tube may be fitted with a pump that is actuated by a push button. When composition is drawn by the pump through to the air mixing or foaming chamber, the desired foam is produced.

Other means for producing foams will be apparent to those skilled in the art. Means for producing aerated foams are described in U.S. Pat. Nos. 4,511,486 and 4,018,364 both of which are hereby incorporated by reference.

Without intending any limitation on the kinds of foaming devices which may be employed in this invention, the applicants have employed a type of foamer that is called an F2 Pumpfoamer. This kind of pump foaming device is manufactured by Airspray, of Pompano Beach, Fla. This device is actuated by a push button and supplies 0.75 ml of composition/stroke or push +/−0.05 ml. Of course, the consumer can control the amount of foam placed on his or her hair through the use of the pump foaming device by the number of strokes of the push button.

The compositions of the invention can be altered to work more efficiently with the particular foaming package or container being employed. One skilled in the art would know how to make such changes within the scope of the present invention.

How to Use Compositions of the Invention

Lightening and/or highlighting and conditioning the hair with the compositions of the invention is carried out by contacting the hair with a composition of the invention, that is, (1) applying water to said hair and (2) applying to said hair a lightening and highlighting effective amount of a conditioning foaming composition of the invention through the use of a foaming spray container; and (3) rubbing said hair with the hands or contacting hair an appliance such as a comb. Alternatively, compositions of the invention can be applied to hair that is damp because it has already been shampooed, or to hair that is dry. When composition is added to hair that is dry, additional water can be added to the hair if desired by the consumer. Foam can be applied throughout the head of hair or to different areas of hair in order to achieve desired patterns of highlighting and hair lightening. A foam is especially useful for doing this because it is easily manipulated by the hands or a hair conditioner implement. Because the consumer can see the foam on his or her head in the mirror one can see and control where on the head the foam is placed. Each application of a composition of the invention results in a small degree of lightening and/or highlighting of the hair. By using a composition of the invention on a daily basis, the hair can be gradually lightened and highlighted until it reaches the desired state. At that point, conditioning with a composition of the invention is ceased, and hair of the desired color has been obtained until it grows out.

A person who uses the conditioner compositions of the invention and also spends time in the sunlight may achieve hair lightening and/or hair highlighting more quickly than someone who uses the compositions of the invention but does not spend time in the sunlight. This is due to the additive effects of the bleaching of hair by sunlight and the chemical action of the conditioning compositions of the invention.

As noted above, compositions of the invention also have the advantage of enabling the user to obtain just the degree of highlighting and/or lightening that he or she desires at which point conditioning of the hair with the compositions of the invention is stopped, and this desired hair coloring will remain until the hair grows out. Once this point is reached the consumer can go back to his or her regular hair conditioning regimen. Another advantage of the compositions of the invention is that they enable the consumer to achieve a gradual lightening of the hair. Thus, if the consumer does not like the direction of the change in color that begins to take place, the consumer can simply stop using the product before a complete color transformation has taken place. In addition, some consumers may want to achieve a large color change as a final result, but they may want to do so gradually because they do not wish to elicit comments from friends and neighbors that can come with a dramatic color change. This gradual change can be achieved with compositions of the invention.

Usually, some lightening or highlighting of the hair will be noticeable within the first about three to about seven consecutive days of conditioning with a composition of the invention. Often, a composition of the invention can be used for up to about 21 consecutive days. However, as mentioned above, an advantage of the invention, is that a composition of the invention may be employed for more or less consecutive days than listed above, as desired by the user. Thus, after 21 days, for example, if the consumer wishes, he or she can continue to use the compositions of the invention if he or she wants his or her hair to become still lighter. In addition, the conditioning compositions may be employed every other day, or at even greater intervals as desired. If compositions of the invention are not employed on consecutive days, use may be made of the consumer's customary non-bleaching conditioner on the days when the bleaching conditioner of the invention is not being used. Because the composition is in the form of a foam, rather than a liquid or cream, it is easier for the consumer to keep said foam composition in the hair, because foam tends to stay in place where applied rather than to drip or run like a liquid or cream. Moreover, the foamable peroxide compositions of the invention are safer to use than liquids, lotions or creams which contain peroxide, because the latter compositions can run or drip and thereby get into the eyes, or onto the skin of the face or scalp, where the peroxide can cause pain and injury.

Compositions of the invention have ingredients which can fall within the following ranges:
  (i) about 0.025% to about 3%, or more preferably from about 0.05% to about 2%, or still more preferably from about 0.1% of a conditioning agent;
  (ii) about 0.1 to about 5%, or more preferably about 1.5 to about 2.5% of a peroxygen compound;
  (iii) about 0.01 to 1.0% an acid, and
  (iv) about 0. 025% to about 3%; more preferably from about 0.05% to about 2%, of a foaming agent.

Where the foaming agent is a cationic surfactant, it will be understood from the discussion above that the cationic surfactant can serve the dual role as both the conditioner and the foaming agent. For example, a composition of the invention can have 1% cationic surfactant and this can serve as both the foaming agent and the conditioner.

The following are examples of specific compositions of the invention which have been made. These examples are not intended to limit the scope of the invention that is being claimed.

EXAMPLES

Example 1 (2.5% Peroxide)

|    | Ingredient                                  | Weight % |
|----|---------------------------------------------|----------|
| 1  | Water                                       | 88.05    |
| 2  | DL-Panthenol, 99%                           | 0.80     |
| 3  | Phosphoric acid, 85%                        | 0.10     |
| 4  | Peg-2 oleamonium chloride & propylene glycol | 0.30    |
| 5  | Cetrimonium chloride, 30%                   | 2.5      |
| 6  | Propylene glycol 100%                       | 0.50     |
| 7  | Kathon CG                                   | 0.05     |
| 8  | DMDM Hydantoin 55%                          | 0.10     |
| 9  | Diazolodinyl urea 100%                      | 0.15     |
| 10 | Sodium dihydrogen phosphate, granular       | 0.20     |
| 11 | Hydrogen peroxide, 35%                      | 7.25     |

The above composition was made by the following steps.
1. Add water to a vessel.
2. Add item 2 through 8 and mix.
3. Add item 8 and 10 and mix until dissolved.
4. Add item 11 and mix until uniform.
measure pH and make sure it is within specifications and adjust with item 3, if necessary.

Example 2 (1.5% Peroxide)

|    | Ingredient                                  | Weight % |
|----|---------------------------------------------|----------|
| 1  | Water                                       | 88.05    |
| 2  | DL-Panthenol, 99%                           | 0.80     |
| 3  | Phosphoric acid, 85%                        | 0.10     |
| 4  | Peg-2 oleamonium chloride & propylene glycol | 0.30    |
| 5  | Cetrimonium chloride, 30%                   | 2.5      |
| 6  | Propylene glycol 100%                       | 0.50     |
| 7  | Kathon CG                                   | 0.05     |
| 8  | DMDM Hydantoin 55%                          | 0.10     |
| 9  | Diazolodinyl urea 100%                      | 0.15     |
| 10 | Sodium dihydrogen phosphate, granular       | 0.20     |
| 11 | water                                       | q.s.     |
| 12 | Hydrogen peroxide, 35%                      | 4.3      |

Mixing Procedure is Analogous to the Mixing Procedure for Example 1

Conditioning compositions of the invention also have the benefit of conditioning the hair at the same time as lightening or highlighting the hair. The conditioning compositions of the invention also have acceptable and very good sensory qualities. They lighten hair; make hair shiny; provide natural-looking and gradual hair highlights; are easy to apply; control how much highlighting the consumer can achieve; enable the consumer to highlight the hair at the places desired; brighten existing highlights; and add shine and body to hair, including darker hair. The compositions of the invention also make hair easier to comb in both the wet and the dry stage. The compositions of the invention also do not leave hair with static and do not cause fly-away hair.

Conditioning compositions of the invention were used and were evaluated by a trained panel of observers and found to lighten and highlight hair. Compositions of the invention were also found to promote ease of detangling and combing in the wet stage. Compositions of the invention were also found to improve hair characteristics in all of the areas set forth in Table 1 below. Test methods for showing hair lightening are given below. Test methods for showing other improvements in hair characteristics are known in the art.

Lightening of Hair Test Methodology for Measurements Given in Table 1

This was a monadic test. A total of 21 females interested in lightening their hair were recruited. Panelists were excluded if they had in excess of 20% gray hair, and currently were highlighting or frosting their hair. All hair colors were allowed. The panelists came to a professional clinic for 5 days in a row. Scalp evaluations were performed by a clinical staff member, prior to any application of the composition. Stylists washed hair and then applied the compositions of example 1 or example 2 to the whole head, leaving a small quarter panel untreated (used only by the chemists to gauge relative color change.) Instrumental measurements of hair lightening were taken using a Minolta Chromameter set to illuminant C. These instrumental measurements were taken on Day 1, prior to any application of the composition and on Day 5 prior to the fifth application of the composition. Panelists completed a daily ballot, recording hair feel and lightening effects on a scale of 1 to 9 as shown in the table below. A score of 9 is the highest score for a given effect or property. A score of 1 is the lowest score for a given effect or property.

The compositions were delivered using a foaming device that is called an F2 Pumpfoamer which has been described herein.

TABLE 1

Means Summary Table for the Total Sample across 5 Days of Testing.

| | Total Sample | | |
|---|---|---|---|
| | n = 56 1.5% Peroxide Example 2 | n = 53 2.5% Peroxide Example 1 | signifi- cant. |
| Wet Stage | | | |
| Ease of detangling | 8.1 | 7.2 | * |
| Ease of combing | 8.1 | 7.2 | * |
| Dry Stage | | | |
| Ease of combing | 7.8 | 7.2 | * |
| Smoothness | 7.9 | 7.4 | |
| Softness | 7.7 | 7.2 | |
| Moisturized | 6.6 | 6.9 | |
| Greasiness | 1.9 | 2.3 | |
| Dryness | 3.0 | 3.5 | |
| Overall conditioning | 7.1 | 6.9 | |
| Coating feel | 3.3 | 3.7 | |
| Shine | 5.4 | 6.4 | * |
| Ease of styling | 7.5 | 7.2 | |
| Body | 6.8 | 6.5 | |
| Flat/limp appearance | 3.4 | 3.2 | |
| Fullness/Volume | 6.1 | 6.5 | |
| Build-up | 2.1 | 2.5 | |
| Lightening-related attributes 1 = none; 9 = a great deal | | | |
| Brightness of hair | 4.8 | 6.1 | * |
| Change of hair color | 3.6 | 5.5 | * |

TABLE 1-continued

Means Summary Table for the Total Sample across 5 Days of Testing.

| | Total Sample | | |
|---|---|---|---|
| | n = 56 1.5% Peroxide Example 2 | n = 53 2.5% Peroxide Example 1 | signifi- cant. |
| Lightening of hair | 3.6 | 5.5 | * |
| Contrasts | 3.7 | 5.4 | * |
| Highlights | 4.3 | 5.5 | * |
| Overall liking | 7.3 | 6.8 | * |

The above test showed that both the Example 1 (2.5% peroxide composition) and Example 2 (1.5% peroxide composition) of the invention produced statistically significant changes as compared to untreated hair for the following characteristics as perceived by the consumers:

Brightness of hair

Change of hair color

Lightening of hair

Contrasts

Highlights.

As can be seen from Table 1 above, the compositions of the invention also brought about improved hair conditioning in the wet stage which was shown by wet combing testing using Instron measurements. Results of consumer panel testing given in Table 1 above also show other conditioning benefits and still other hair benefits beyond conditioning that were obtained through the use of two compositions of the invention. Moreover, still other consumer testing not given in Table 1 above shows that the compositions of the invention performed at parity as conditioners with a commercial (non-lightening and non-highlighting) conditioner.

Test Methodology for the Results Given in Tables 2 and 3

Two leave-in conditioners the Example 1 (2.5% peroxide composition) and Example (1.5% peroxide composition) were tested in a salon study. Instrumental measurements of lightness (color) were made before the first application of conditioner and after the fourth application of conditioner.

Color measurements were made with a Minolta Chromameter set to illuminant C. Ten readings of L* (lightness) measurements were averaged for every value reported; two sets of measurements were made at each time point.

Measurements were taken close to the crown of the head and thus on relatively new growth hair. A "map" of each head was made to ensure that the same area was measured at both time points.

Eleven subjects were treated with Example 1 (2.5%, peroxide composition) and Example 2 (1.5%, peroxide composition) (Table 2) and eleven with the with Example 1 (2.5%, peroxide composition) (Table 3).

RESULTS

The L* values measured before treatment and after four treatments are given in Tables 2 and 3. The duplicate measurements (10 readings each) and their averages are listed.

TABLE 2

L* Values Before and After Treatment With 1.5% peroxide (Example 2) Leave-In Conditioner

| panelist # | Before treatment | | | After treatment | | | ΔL* |
|---|---|---|---|---|---|---|---|
| | 1st | 2nd | Average | 1st | 2nd | Average | |
| 1 | 24.9 | 22.5 | 23.7 | 25.2 | 25.2 | 25.2 | 1.5 |
| 3 | 43.0 | 43.0 | 43.0 | 44.3 | 43.8 | 44.1 | 1.1 |
| 5 | 22.3 | 22.6 | 22.5 | 25.0 | 26.7 | 25.8 | 3.3 |
| 7 | 35.5 | 35.4 | 35.4 | 44.1 | 43.5 | 43.8 | 8.4 |
| 9 | 23.9 | 23.5 | 23.7 | 25.2 | 24.0 | 24.6 | 0.9 |
| 11 | 31.8 | 31.5 | 31.6 | 32.4 | 32.0 | 32.2 | 0.6 |
| 13 | 19.5 | 19.8 | 19.6 | 19.7 | 19.4 | 19.5 | −0.1 |
| 15 | 33.5 | 34.1 | 33.8 | 35.2 | 34.9 | 35.0 | 1.2 |
| 17 | 34.4 | 34.0 | 34.2 | 35.5 | 35.5 | 35.5 | 1.3 |
| 23 | 20.8 | 20.8 | 20.8 | 22.4 | 22.5 | 22.4 | 1.6 |
| 25 | 40.8 | 43.0 | 41.9 | 51.9 | 52.9 | 52.4 | 10.5 |

TABLE 3

L* Values Before and After Treatment With 2.5% peroxide (Example 1) Leave-In Conditioner

| panelist # | Before treatment | | | After treatment | | | ΔL* |
|---|---|---|---|---|---|---|---|
| | 1st | 2nd | Average | 1st | 2nd | Average | |
| 2 | 30.2 | 30.8 | 30.5 | 39.6 | 38.9 | 39.3 | 8.8 |
| 4 | 40.9 | 40.5 | 40.7 | 46.9 | 46.7 | 46.8 | 6.1 |
| 6 | 29.1 | 28.8 | 28.9 | 30.5 | 30.5 | 30.5 | 1.6 |
| 8 | 31.9 | 31.5 | 31.7 | 37.3 | 37.7 | 37.5 | 5.8 |
| 10 | 48.6 | 48.8 | 48.7 | 53.5 | 53.9 | 53.7 | 5.0 |
| 12 | 36.6 | 36.6 | 36.6 | 38.7 | 39.2 | 39.0 | 2.4 |
| 16 | 20.3 | 20.5 | 20.4 | 21.5 | 19.5 | 20.5 | 0.1 |
| 20 | 22.6 | 22.7 | 22.7 | 24.7 | 24.8 | 24.8 | 2.1 |
| 22 | 21.5 | 21.5 | 21.5 | 23.0 | 22.7 | 22.8 | 1.3 |
| 24 | 21.5 | 21.8 | 21.7 | 22.6 | 22.7 | 22.7 | 1.0 |
| 26 | 29.1 | 29.3 | 29.2 | 28.6 | 28.5 | 28.6 | −0.6 |

Significant lightening of hair occurred after four treatments with either a 1.5% and a 2.5% leave-in conditioner, as measured instrumentally.

A large majority of panelists showed an increase in lightness (8 out of 11 for the 1.5% conditioner and 9 out of 11 for the 2.5% conditioner.)

Measurements were made on the crown of the head, an area likely to show less ligthening than on tip end hair.

Although the average increase in lightness was similar for the two conditioners, the number of subjects showing a large increase in lightness (ΔL*>3) is greater for the 2.5% conditioner.

Hair that is initially lighter in color generally lightens to a greater degree with conditioner use than hair that is darker.

In comparing the performance of the 1.5% and the 2.5% conditioners, it is seen that a larger number of panelists show a large (>3) increase in L* with the higher peroxide conditioner.

Changes in lightness that occurred were statistically significant.

Test Methodology for Tables 4 and 5 Change in Hair Lightening (ΔL) Brought About by Two Compositions of the Invention for Differing Hair Colors Two leave-in conditioners (at 1.5% and 2.5% peroxide) were tested in a salon study. Instrumental measurements of lightness (color) were made before the first application and after the fourth application. Color measurements were made with a Minolta Chromameter set to illuminant C. Ten readings of L* (lightness) measurements were averaged for every value reported; two sets of measurements were made at each time point.

TABLE 4

Comparison of Initial State of Hair to ΔL* for the 1.5% Conditioner-A test of hair with different colors
1.5% leave-in conditioner

| panelist | | initial L* | ΔL* |
|---|---|---|---|
| 1 | dyed dark brown | 23.7 | 1.5 |
| 3 | medium blonde | 43.0 | 1.1 |
| 5 | medium brown (perm) | 22.5 | 3.3 |
| 7 | dark blonde/Sun-In | 35.4 | 8.4 |
| 9 | dark brown/gray | 23.7 | 0.9 |
| 11 | dyed red | 31.6 | 0.6 |
| 13 | black | 19.6 | −0.1 |
| 15 | light brown | 33.8 | 1.2 |
| 17 | dyed red | 34.2 | 1.3 |
| 23 | dark brown | 20.8 | 1.6 |
| 25 | dark brown dyed to blond | 41.9 | 10.5 |

TABLE 5

Comparison of Initial State of Hair to ΔL* for the 2.5% Conditioner
2.5% leave-in conditioner

| panelist | | initial L* | ΔL* |
|---|---|---|---|
| 2 | dyed auburn | 30.5 | 8.8 |
| 4 | medium blonde | 40.7 | 6.1 |
| 6 | red/auburn | 29.0 | 1.6 |
| 8 | light brown | 31.7 | 5.8 |
| 10 | light blonde/dyed | 48.7 | 5.0 |
| 12 | light red | 36.6 | 2.4 |
| 16 | dyed medium brown | 20.4 | 0.1 |
| 20 | dark brown | 22.6 | 2.1 |
| 22 | dyed dark brown | 21.5 | 1.3 |
| 24 | dark brown | 21.7 | 1.0 |
| 26 | dyed chestnut | 29.2 | −0.6 |

SUMMARY OF TEST RESULTS

Significant lightening of hair occurs after four treatments with either a 1.5% and a 2.5% leave-in conditioner, as measured instrumentally.

A large majority of panelists show an increase in lightness (8 out of 11 for the, 1.5% conditioner and 9 out of 11 for the 2.5% conditioner.)

Measurements were made on the crown of the head, an area likely to show less lightening than on tip end hair.

Although the average increase in lightness was similar for the two conditioners, lo the number of subjects showing a large increase in lightness (ΔL*>3) is greater for the 2.5% conditioner.

Hair that is initially lighter in color generally lightens to a greater degree with conditioner use than hair that is darker.

What is claimed is:

1. A foaming product for hair comprising:
   (A) an aqueous, foamable composition comprising:
   (i) from about 0.025% to about 3% by weight of the composition of a conditioning agent;
   (ii) from about 0.1 to about 5% by weight of the composition of a peroxygen compound;
   (iii) from about 0.01% to about 1% by weight of the composition of an acid; and (iv) from about 0.025% to about 3% by weight of the composition cationic surfactant foaming agent;

wherein said composition has a pH of about 5 or less;

(B) a foam dispensing device charged with the foamable composition, the device comprising a foaming chamber communicating with a homogenizing element interposed between an air-mixing chamber and a discharge orifice; and wherein the product delivers a foamed composition to areas of the hair in a pattern manipulated by a consumer to gradually lighten or highlight the hair.

2. A product according to claim 1, wherein said cationic surfactant is a cetrimonium salt.

3. A product according to claim 1, wherein the cationic surfactant is present in an amount from 0.75 to about 3% by weight of the composition.

4. A product according to claim 1, wherein the conditioning agent is a quaternary amine compound.

5. A product according to claim 4, wherein the quaternary amine compound is a PEG oleamonium salt.

6. A product according to claim 1, wherein said composition further comprises a zwitterionic surfactant which is a derivative of a quaternary ammonium, phosphonium, or sulfonium compound having aliphatic radicals wherein the aliphatic radicals are straight or branched chain and one of the aliphatic radicals contain from 8 to 18 carbon atoms.

7. A product according to claim 1, wherein said composition further comprises an amphoteric surfactant which is selected from the group consisting of sodium 3-dodecylamino propionate, sodium 3-dodecylaminopropane sulfonate, and sodium lauryl sarcosinate.

* * * * *